United States Patent
Yang et al.

(10) Patent No.: US 8,722,945 B2
(45) Date of Patent: *May 13, 2014

(54) METHOD FOR PRETREATING AND REGENERATING CATALYSTS USED IN A PROCESS FOR MAKING FLUOROIODOALKANES

(75) Inventors: Shuwu Yang, Richmond, CA (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 795 days.

This patent is subject to a terminal disclaimer.

(21) Appl. No.: 12/264,635

(22) Filed: Nov. 4, 2008

(65) Prior Publication Data

US 2009/0137852 A1 May 28, 2009

Related U.S. Application Data

(60) Provisional application No. 61/004,488, filed on Nov. 28, 2007.

(51) Int. Cl.
*C07C 261/00* (2006.01)
(52) U.S. Cl.
USPC .......................................................... 570/137
(58) Field of Classification Search
None
See application file for complete search history.

(56) References Cited

U.S. PATENT DOCUMENTS

| | | | |
|---|---|---|---|
| 5,892,136 A * | 4/1999 | Nagasaki et al. | 570/174 |
| 6,977,316 B1 | 12/2005 | Mukhopadhyay et al. | |
| 7,071,367 B1 | 7/2006 | Mukhopadhyay et al. | |
| 7,196,236 B2 * | 3/2007 | Mukhopadhyay et al. | 570/174 |
| 2006/0122440 A1 * | 6/2006 | Mukhopadhyay et al. | 570/152 |
| 2008/0200735 A1 * | 8/2008 | Yang et al. | 570/174 |

FOREIGN PATENT DOCUMENTS

| | | |
|---|---|---|
| JP | 52-068110 | 6/1977 |
| JP | 10-204006 | 8/1998 |
| JP | 2005-008543 | 1/2005 |
| JP | 2008-523089 | 7/2008 |

OTHER PUBLICATIONS

Nagasaki et al. Catalyst Today 88 (2004) 121-126.*
JP Office Action—Japanese Patent Application No. 2008-301910 (English Translation).

* cited by examiner

*Primary Examiner* — Brandon Fetterolf
*Assistant Examiner* — Blaine G Doletski
(74) *Attorney, Agent, or Firm* — Bruce O. Bradford

(57) ABSTRACT

A process for the preparation of a fluoroiodoalkane represented by the structural formula $CF_3(CF_2)_n$—I, wherein n is 0 or 1. The process has the step of reacting a source of iodine with a compound represented by the structural formula $CF_3(CF_2)_n$—Y, wherein Y is selected from H, Cl, Br and COOH and wherein n is 0 or 1. The reaction is carried out at a temperature from about 100° C. to about 750° C. and at a pressure from about 0.001 to about 100 atm for a contact time from about 0.001 second to about 300 hours in the presence a catalyst. The catalyst is subject to one or both of the following: (a) treating the catalyst prior to the reaction via contact with a gas selected from the group consisting of hydrogen fluoride, trifluoromethane, hydrogen, hydrogen iodide, iodine, fluorine, and oxygen, wherein the contact is carried out at a temperature and for a contact time sufficient to reduce the length of the induction period of the catalyst; and (b) treating the catalyst after the reaction via contact with a gas selected from the group consisting of hydrogen fluoride, hydrogen, fluorine, oxygen, or air at a temperature and for a contact time sufficient to regenerate the catalyst.

32 Claims, No Drawings

METHOD FOR PRETREATING AND REGENERATING CATALYSTS USED IN A PROCESS FOR MAKING FLUOROIODOALKANES

CROSS-RELATED APPLICATION

This application claims priority from U.S. Provisional Patent Application, Ser. No. 61/004488, filed on Nov. 28, 2007, which is incorporated herein by reference in its entirety.

BACKGROUND

1. Field of the Disclosure

The present disclosure relates to a process for making fluoroiodoalkanes. The present disclosure further relates to methods for pretreating and regenerating catalysts used in a process for making fluoroiodoalkanes.

2. Description of the Related Art

Trifluoroiodomethane ($CF_3I$) and pentafluoroiodoethane ($C_2F_5I$) have been used as synthesis intermediates in preparing fluorinated compounds. Trifluoroiodomethane is also being considered as a substitute fire extinguishing agent for trifluorobromomethane and as a refrigerant with low global warming potential in blends with hydrofluorocarbons.

Trifluoroiodomethane and pentafluoroiodoethane can be prepared by reacting iodine with trifluoromethane ($CF_3H$), pentafluoroethane ($CF_3CF_2H$) or trifluoroacetic acid ($CF_3COOH$) over a solid catalyst in the presence or absence of oxygen. Oxygen has been co-fed in such reactions to reduce the level and/or rate of catalyst deactivation resulting from the formation of carbon on the surface of the catalyst. However, co-feeding of oxygen has not been completely effective in preventing catalyst deactivation. Another problem encountered with the catalyst is the lengthy induction period required to reach reaction steady state.

It would be desirable to have a process for making iodofluoroalkanes in which a reduced level and/or rate of catalyst deactivation is exhibited. It would further be desirable to have a process for catalyst pretreatment so that the induction period is shortened. Furthermore, due to the easy catalyst deactivation during reaction, it would be most desirable to have a process to regenerate used catalyst so that its original activity is restored.

SUMMARY

According to the present disclosure, there is a process for the preparation of a fluoroiodoalkane represented by the structural formula:

$CF_3(CF_2)_n$—I wherein n is 0 or 1. The process has the step of reacting a source of iodine with a compound represented by the structural formula:

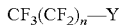
$CF_3(CF_2)_n$—Y wherein Y is selected from H, Cl, Br and COOH and wherein n is 0 or 1. The reaction is carried out at a temperature of about 100° C. to about 750° C. at a pressure of about 0.001 to about 100 atm for a contact time of about 0.001 second to about 300 hours in the presence a solid catalyst. The catalyst is subject to one or both of the following treatments:

a) treating the catalyst prior to the reaction (pretreatment) via contact with a gas selected from the group consisting of hydrogen fluoride, trifluoromethane, hydrogen, hydrogen iodide, iodine, fluorine, and oxygen, wherein the contact is carried out at a temperature and for a contact time sufficient to reduce the length of the induction period of the catalyst; and b) treating the catalyst after the reaction (regeneration) via contact with a gas selected from the group consisting of hydrogen fluoride, hydrogen, fluorine, oxygen, or air at a temperature and for a contact time sufficient to regenerate the catalyst.

DETAILED DESCRIPTION OF THE PREFERRED EMBODIMENT

This disclosure discloses pretreatment and regeneration methods for catalysts used in a process of making fluoroiodoalkanes, such as trifluoroiodomethane ($CF_3I$) and pentafluoroiodoethane ($C_2F_5I$). The methods can increase reaction conversion, enhance selectivity for particular desired product compounds, and reduce or eliminate induction periods for catalysts. The pretreatment and regeneration methods can be used alone or in conjunction with each other in the process for making the fluoroiodoalkanes.

The process of the present disclosure is useful in making fluoroiodoalkane compounds represented by the following structural formula:

$CF_3(CF_2)_n$—I wherein n is 0 or 1. Preferred fluoroiodoalkane compounds include trifluoroiodomethane and pentafluoroiodoethane.

The fluoroiodoalkane compounds are prepared by reacting a source of iodine with a precursor compound represented by the following structural formula:

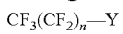
$CF_3(CF_2)_n$—Y wherein Y is selected from H, Cl, Br and COOH and wherein n is 0 or 1. The precursor compound represented by the formula $CF_3(CF_2)_n$—Y can be, for example, $CF_3H$ (trifluoromethane), $CF_3CF_2H$ (1,1,1,2,2-pentafluoroethane), $CF_3COOH$ (trifluoroacetic acid), $CF_3Cl$ (chlorotrifluoromethane), $CF_3Br$ (bromotrifluoromethane), and combinations thereof. Useful sources of iodine include $I_2$ (iodine), HI (hydrogen iodide), ICl (iodine chloride), $IF_5$ (pentafluoroiodine), $CI_4$ (tetraiodomethane), and combinations thereof. The process can optionally employ along with the reactants a diluent, such as an inert gas, CO, $CO_2$, water, an organic solvent, or a mixture thereof. The diluent refers to an inert gas or liquid used to dilute and carry the reactants.

The iodination reaction may be carried out in the presence or absence of a source of oxygen, such as $O_2$, air, $O_3$ (ozone), $N_2O$ (dinitrogen oxide), $H_2O_2$ (hydrogen peroxide), and combinations thereof. Oxygen can optionally be included to assist in reduction of carbon buildup on catalyst surfaces, and hence, reduction in catalyst deactivation. Oxygen reacts with carbon to form carbon monoxide/dioxide, which effectively reduces carbon buildup.

The iodination reaction is preferably carried out at temperatures from about 100° C. to about 750° C., preferably from about 300° C. to about 600° C., and more preferably from 400 to 500° C. The iodination reaction is preferably carried out at pressures from about 0.001 atmosphere (atm) to about 100 atm, preferably at about 0.01 to about 20 atm, and more preferably at about 0.5 to about 5 atm. The iodination reaction is preferably carried out for a contact time of from about 0.001 second to about 300 hours, more preferably from about 0.1 second to about 1 hour, and most preferably from about 1 sec to about 10 minutes. Contact time is defined as the ratio of the catalyst bed volume to the flow rate of the reactant or treatment gas (or gas mixture). While pretreatment time or regeneration time is the length of time the treatment gas or gas mixture is held in direct contact with a catalyst.

One aspect of the present disclosure is pretreatment of the catalyst. In pretreatment, the catalyst can be contacted with HF (hydrogen fluoride), $H_2$ (hydrogen), $CF_3H$ (trifluoromethane), HI (hydrogen iodide), $I_2$ (iodine), $F_2$ (fluorine), $O_2$ (oxygen), or air. The pretreating gas can be pure or be diluted with an inert gas, such as $N_2$ (nitrogen), Ar (argon), or He (helium). The pretreatment takes place at a temperature and for a contact time sufficient to reduce the length of the induction period of the catalyst. The pretreatment preferably takes place at a temperature of about 100° C. to about 600° C. and most preferably about 200° C. to about 500° C. The pretreatment preferably has a contact time of about 0.001 second to about 1 hour, more preferably about 0.1 second to 10 minutes, and most preferably about 1 second to 5 minutes.

The pretreatment preferably takes place in a pretreatment time of about 10 minutes to about 100 hours, more preferably about 30 minutes to about 20 hours, and most preferably about 1 hr to about 10 hrs. The catalysts used for this reaction usually have an induction period. During an induction period, the catalysts exhibit little or no activity in forming desired products. After the catalysts have run for certain length of time, desired products begin to form. The catalyst pretreatment procedures described herein provide an advantage of reducing the length of the induction period for the catalyst. During the pretreatment, the catalyst's chemical state is changed, from its original state, usually a salt, to metal, metal oxide, metal fluoride, or metal iodide, which exhibits different reactivity (e.g., shorter induction period, higher activity) as its original state. After pretreatment and before iodination, the catalyst is optionally purged with an inert gas at reaction temperature for about 0.5 to about 2 hrs.

Another aspect of the present disclosure is regeneration of the used catalyst. After a catalyst has been run for a certain amount of time, catalyst deactivation takes place due to the formation of carbon on the catalyst. In this case, the reaction was stopped and the catalyst was regenerated in the same reactor. Preferably, a used catalyst was first purged with an inert gas such as nitrogen at 200° C. to 500° C. for up to 300 hrs. Subsequently, the reactor was set at desired regeneration temperature, and the used catalyst is contacted with hydrogen fluoride, hydrogen, fluorine, oxygen, or air. The regenerating gas can be pure or diluted with an inert gas, such as nitrogen, helium, or argon. The regeneration takes place at a temperature and for a contact time sufficient to regenerate the catalyst. The regeneration preferably takes place at a temperature of about 100° C. to about 600° C., more preferably about 200° C. to about 500° C., and most preferably from about 350° C. to about 450° C. Contact time of regeneration gas with used catalysts ranges from 0.0001 sec to 300 hours, preferably from about 0.001 seconds to about 100 hours and more preferably from about 0.01 seconds to about 50 hours. The regeneration time varies from about 0.01 seconds to about 150 hrs, preferably from about 2 to about 30 hrs, and more preferably from about 5 to about 15 hrs. A preferred pressure for regeneration is atmospheric. Regeneration provides the advantage of partially or substantially restoring the activity of the catalyst to its original level. For catalyst regeneration using hydrogen, the existence of a small amount of a noble metal (e.g., Pt and Pd) in the catalyst is preferred in order to more effectively initiate a methanation reaction ($C+2H_2=CH_4$). After regeneration, the catalyst may optionally be purged with an inert gas at reaction temperature for about 0.5 to about 2 hrs.

The pretreatment and regeneration of the catalyst are separable aspects of the disclosure and each can be carried out independently of the other in conjunction with the iodination reaction. Preferably, both are carried out. If desired, the sequence of pretreatment, iodination, and regeneration can be repeated consecutively as many times as desired (two or more times) with the same catalyst.

Catalysts used in the process of the present disclosure are any of those known in the art as useful for synthesizing fluoroiodoalkanes. Such catalysts include, but are not limited to, the following: alkali metals (Li, Na, K, Rb and Cs), alkaline earth metals (Be, Mg, Ca, Sr and Ba), transition metals (Sc, Y, V, Cr, Mn, Mo, Cu, Zn, and the like), lanthanides or rare earth metals (La, Ce, Pr, Nd, Pm, Sm, Eu, Gd, Tb, Dy, Ho, Er, Tm, Yb, Lu), and mixtures or combinations thereof. The metals may take any of their existing states and forms, such as oxides, nitrates, halides, carbonates, bicarbonates, sulfates, and phosphates thereof (metal salts). Particularly preferred catalysts include K (potassium), $KNO_3$ (potassium nitrate), $K_3PO_4$ (potassium phosphate), Cs (cesium) and $La(NO_3)_3$ (Lanthanum nitrate). Catalysts may be supported or unsupported. Supported catalysts are preferred. A preferred support substrate is an activated carbon.

The reactor type can be a fixed bed reactor or a moving bed reactor, such as fluidized bed reactor, rotary reactor, rising bed reactor, or a combination thereof. The process can be either a batch or continuous.

The following are examples of the present disclosure and are not to be construed as limiting.

EXAMPLES

Fluoroiodoalkanes were prepared in accordance with the present disclosure. Catalysts were prepared and pretreated prior to reaction. The catalysts were then regenerated after reaction and additional fluoroiodoalkanes were prepared.
Preparation of Carbon Supported Potassium Salt (K/C) Catalysts and Lanthanum Oxide or Salt ($La_2O_3$/C) Catalysts:

Designated amount of $KNO_3$ or $La(NO_3)_3$ was dissolved in deionized water (the amount of water was calculated from the pore volume of a support). After the salts were dissolved completely, a designated amount of activated carbon (pre-dried at 100° C. to 120° C. for 12 hours (hr) was slowly poured into the solution, or vice versa. The paste was stirred continuously to achieve homogeneous impregnation and then was put in a hood overnight to allow adequate impregnation. Subsequently the impregnated sample was dried in an oven at 100° C. to 120° C. for 12 hr and calcined at 450° C. to 550° C. for 4 hr under a stream of nitrogen.
Preparation of Promoted K/C Catalysts:

A designated amount of $KNO_3$ and a designated amount of a precursor of a promoter (e.g., $La(NO_3)_3$), were dissolved in a pre-determined amount of deionized water. After all salts were dissolved completely, a designated amount of activated carbon (pre-dried at 100° C. to 120° C. for 12 hr) was slowly poured into the solution, or vice versa. The resulting paste was stirred continuously to achieve homogeneous impregnation and then was placed in a hood overnight to allow homogenous impregnation. Subsequently, the impregnated sample was dried in an oven at about 100° C. to 120° C. for 12 hr and thereafter was calcined at 450° C. to 550° C. for 4 hr under a stream of nitrogen.

The activated carbon support used was pelletized Shirasagi C2X 4/6-2 (Japan EnviroChemicals, Ltd.), a highly purified activated carbon support with a surface area above 1000 $m^2$/g and an average pore diameter of 23 Å.

About 50 ml of calcined catalyst were loaded in a Hastelloy C pipe reactor with inner diameter of ½ inch. The temperature of the reactor was measured by a 5-point thermocouple bundle (4 inch spacing between thermocouples) accommodated in a thermowell in the center of the reactor. Before reaction, the catalyst was first pretreated with a gas or gas mixture at the conditions given in the examples below. After pretreatment, reactants, including $CF_3H$ and iodine ($I_2$) with or without oxygen were introduced. Unreacted reactants and products were analyzed by on-line gas chromatography. When the catalyst was deactivated after reaction for a certain amount of time, the catalyst was regenerated per the methods described below.

Example 1

Reactivity of Catalysts Pretreated in Different Environments

Table 1 lists the reactivity of K—$La_2O_3$/C catalyst pretreated under various conditions. For the catalyst that was normally treated with $N_2$ at 500° C. for 2 hrs before reaction, it showed a two-hour induction period. In the presence of oxygen ($O_2$/$CF_3H$=0.1), it gave a 52.6% $CF_3H$ conversion, a 51.2% $CF_3I$ selectivity and a 3.3% $CF_3CF_2I$ selectivity. In the absence of co-fed oxygen ($O_2$/$CF_3H$=0), the catalyst had a 43.0% $CF_3H$ conversion, a 73.4% $CF_3I$ selectivity an a 4.1% $CF_3CF_2I$ selectivity after 8 hours on stream. When the catalyst was pretreated with $CF_3H$ at 500° C. for 2 hrs, the induction period of the catalyst disappeared, and the catalyst gave a 50.7% $CF_3H$ conversion, a 52.0% $CF_3I$ selectivity and a 3.3% $CF_3CF_2I$ selectivity, identical to those of the catalyst pretreated with $N_2$. Treating the catalyst with $H_2$ or $I_2$ prolonged the induction period to 4 hrs, but the catalyst reactivity did not change much compared to the catalyst normally treated with $N_2$.

TABLE 1

(Reactivity of pretreated K—$La_2O_3$/C catalyst)

| Pretreatment condition | $O_2$/$CF_3H$ molar ratio | Induction period (h) | $CF_3H$ conversion (%) | $CF_3I$ selectivity (%) | $CF_3CF_2I$ selectivity (%) |
|---|---|---|---|---|---|
| $N_2$/500° C./ 2 hrs | 0.1 | 2 | 52.6 | 51.2 | 3.3 |
| | 0 | 2 | 43.0 | 73.4 | 4.1 |
| $CF_3H$/ 500° C./ 2 hrs | 0.1 | 0 | 50.7 | 52.0 | 3.3 |
| $H_2$/300° C./ 2 hrs | 0 | 4 | 42.8 | 71.3 | 4.4 |
| $I_2$/500° C./ 2 hrs | 0.1 | 4 | 49.7 | 50.7 | 3.6 |

*Reaction conditions: 500° C., $I_2$/$CF_3H$ (molar ratio) = 0.33, contact time: 20 seconds (s). Reaction time: 8 hr.

Example 2

Catalyst Regeneration—Effect of Regeneration Temperature

In the absence of co-fed oxygen, the catalyst activity decreased rapidly due to the formation of carbon during the reaction. As shown in Table 2, fresh K—$La_2O_3$/C exhibited an initial activity of 58%. After 10 hours on stream, the catalyst activity dropped to 36.4%. In order to regenerate the deactivated catalyst, a used catalyst was treated in a mixture of $O_2$ in $N_2$ under designated conditions. Table 2 listed the activity of used catalysts regenerated with 10% $O_2$—$N_2$ (10% by volume in oxygen/nitrogen mixture) at various temperatures for 10 hrs. The catalyst regenerated at 400° C. gave 70.6% $CF_3H$ conversion, which was even higher than the initial activity of the fresh catalyst (58.0%). The catalyst regenerated at 450° C. exhibited 48.6% $CF_3H$ conversion, which was significantly higher than the activity of the deactivated catalyst (36.4%) and slightly lower than the initial activity of the fresh catalyst (58.0%). For the catalyst pretreated with 10% $O_2$—$N_2$ at 500° C., catalyst activity was only restored slightly, from 36.4% to 39%. These results clearly suggested that 400° C. was a better regeneration temperature than 450 and 500° C. When the catalyst was regenerated with 5% $O_2$—$N_2$ at 400° C. for 10 hours, the catalyst activity was restored to 60.5% from 36.4%.

TABLE 2

(Reactivity of used K—$La_2O_3$/C catalyst regenerated with 10 vol. % $O_2$—$N_2$ for 10 hrs at various temperatures)

| | Regeneration Conditions | | | |
|---|---|---|---|---|
| Catalyst | Temperature (° C.) | Time (h) | $O_2$ volume concentration in $O_2$—$N_2$ | $CF_3H$ conversion (%) |
| Fresh (2 h) | / | / | / | 58.0 |
| Fresh (10 h) | / | / | / | 36.4 |
| Used | 400 | 10 | 10% | 70.6 |
| | 450 | 10 | 10% | 48.6 |
| | 500 | 10 | 10% | 39.0 |
| | 400 | 10 | 5% | 60.5 |

*Reaction conditions: 500° C., $I_2$/$CF_3H$ (molar ratio) = 0.33, $O_2$/$CF_3H$ (molar ratio) = 0, contact time: 20 s.

Example 3

Catalyst Regeneration—Effect of Oxygen Concentration

The effect of oxygen volume concentration in $O_2$—$N_2$ was investigated and the results are set forth in Table 3. When the oxygen concentration in $O_2$—$N_2$ was 2%, the catalyst could not be regenerated at 450° C. When the oxygen concentration increased to 5% or 10%, the catalyst activity was partially restored. Compared with the results in Table 2, it is apparent that the catalyst could be regenerated better in 10% $O_2$—$N_2$ than in 5% $O_2$—$N_2$ when the regeneration temperature was 400° C.

TABLE 3

(Reactivity of used K—$La_2O_3$/C catalyst regenerated at 450° C. for 10 hrs with various $O_2$ concentrations in $N_2$)

| | Regeneration Conditions | | | |
|---|---|---|---|---|
| Catalyst | Temperature (° C.) | Time (h) | $O_2$ volume concentration in $O_2$—$N_2$ | $CF_3H$ conversion (%) |
| Fresh (2 h) | / | / | / | 58.0 |
| Fresh (10 h) | / | / | / | 36.4 |
| Used | 450 | 10 | 2% | 34.5 |
| | 450 | 10 | 5% | 49.9 |
| | 450 | 10 | 10% | 48.6 |

*Reaction conditions: 500° C., $I_2$/$CF_3H$ (molar ratio) = 0.33, $O_2$/$CF_3H$ (molar ratio) = 0, contact time: 20 s.

Example 4

Catalyst Regeneration—Effect of Regeneration Time

Catalyst was regenerated with 10% $O_2$—$N_2$ at 450° C. for varying lengths of time. The activity of the used catalyst appeared to increase with regeneration time, suggesting the continuous removal of coke formed on the used catalyst. The results are set forth in Table 4.

TABLE 4

(Effect of regeneration time on the reactivity of used K—$La_2O_3$/C catalyst regenerated with 10 vol. % $O_2$—$N_2$ at 450° C.)

| | Regeneration Conditions | | | |
|---|---|---|---|---|
| Catalyst | Temperature (° C.) | Time (hr) | $O_2$ volume concentration in $O_2$—$N_2$ | $CF_3H$ conversion (%) |
| Fresh (2 hr) | / | / | / | 58.0 |
| Fresh (10 hr) | / | / | / | 36.4 |
| Used | 450 | 5 | 10% | 45.2 |
| | 450 | 10 | 10% | 48.6 |
| | 450 | 15 | 10% | 51.5 |

*Reaction conditions: 500° C., $I_2$/$CF_3H$ (molar ratio) = 0.33, $O_2$/$CF_3H$ (molar ratio) = 0, contact time: 20 s.

Example 5

Regeneration of Used Catalysts with Different Compositions

Catalysts of different compositions were regenerated and tested for activity. Catalysts K—$La_2O_3$/C, Pd/K—$La_2O_3$/C, K—Cs/C, and $K_3PO_4$/C, were regenerated at the same conditions. When 1 wt. % Pd was added to K—$La_2O_3$/C, $CF_3H$ conversion of the regenerated catalyst was 50.6% (versus 35.0% before regeneration). Fresh K—Cs/C exhibited 68.8% $CF_3H$ conversion and 38.1% $CF_3I$ selectivity in the beginning of the reaction (3 hr) and its activity dropped to 39.4% after 10 hours on stream. After regeneration with 10% $O_2$—$N_2$ at 450° C. for 10 hours, the catalyst exhibited 49.8% $CF_3H$ conversion. For K/C using $K_3PO_4$ as a potassium source, the used catalyst exhibited nearly the same initial activity as the fresh catalyst did. The results are set forth in Table 5 below.

TABLE 5

(Reactivity of different used catalysts regenerated at 450° C. for 10 hrs with 10% $O_2$—$N_2$)

| Catalyst | Fresh or regenerated | $CF_3H$ conversion (%) | $CF_3I$ selectivity (%) | $CF_3CF_2I$ selectivity (%) |
|---|---|---|---|---|
| 7.5% K—5% $La_2O_3$/C | Fresh (2 hr) | 58.0 | 62.2 | 3.6 |
| | Fresh (10 hr) | 36.4 | 76.9 | 3.6 |
| | Regenerated | 48.6 | 66.6 | 4.2 |
| 1% Pd/7.5% K—5% $La_2O_3$/C | Fresh (3 hr) | 52.3 | 64.4 | 4.0 |
| | Fresh (10 hr) | 35.0 | 75.4 | 4.2 |
| | Regenerated | 50.6 | 50.4 | 2.5 |
| 1.7% K—5.8% Cs/C | Fresh (3 hr) | 68.8 | 38.1 | 1.6 |
| | Fresh (10 hr) | 39.4 | 64.4 | 2.4 |
| | Regenerated | 49.8 | 52.1 | 2.7 |
| 7.5% K($K_3PO_4$)/C | Fresh (4 hr) | 48.7 | 66.1 | 3.5 |
| | Fresh (10 hr) | 37.6 | 67.9 | 2.7 |
| | Regenerated | 47.3 | 60.7 | 2.7 |

*Reaction conditions: 500° C., $I_2$/$CF_3H$ (molar ratio) = 0.33, $O_2$/$CF_3H$ (molar ratio) = 0, contact time: 20 s.

From the foregoing, it is apparent that the induction period of a catalyst can be decreased and the activity of used catalyst can be restored using the pretreatment and regeneration steps of the present disclosure.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances which fall within the scope of the appended claims.

What is claimed is:

1. A process for the preparation of a fluoroiodoalkane represented by the structural formula $$CF_3(CF_2)_n—I$$

wherein n is 0 or 1, consisting essentially of:
reacting a source of iodine with a compound represented by the structural formula $$CF_3(CF_2)_n—Y$$

wherein Y is selected from H, Cl, Br and COOH and wherein n is 0 or 1, wherein the reaction is carried out at a temperature and at a pressure and for a contact time in the presence a catalyst sufficient to prepare the fluoroiodoalkane, and wherein the catalyst is subject to one or both of the following steps:
a) treating the catalyst prior to the reaction via contact with a gas selected from the group consisting of hydrogen fluoride, trifluoromethane, hydrogen, hydrogen iodide, iodine, and fluorine, at a temperature and for a contact time sufficient to reduce the length of the induction period of the catalyst; and
b) treating the catalyst after the reaction via contact with a gas selected from the group consisting of hydrogen fluoride, hydrogen, and fluorine, at a temperature and for a contact time sufficient to regenerate the catalyst.

2. The process of claim 1, wherein the catalyst is subject to both steps a) and b).

3. The process of claim 2, wherein step b) is repeated.

4. The process of claim 1, wherein step a) is carried out at a temperature between about 100° C. and about 600° C. for a contact time of about 0.001 seconds to about 1 hour and for a length of time of about 10 minutes to about 100 hours, and wherein step a) is optionally followed by contacting the catalyst with an inert gas for about 0.5 hours to about 2 hours or more.

5. The process of claim 4, wherein step a) is carried out at a temperature between about 200° C. and about 500° C. for a contact time of about 0.1 seconds to about 10 minutes and for a length of time of about 30 minutes to about 20 hours, and wherein step a) is optionally followed by contacting the catalyst with an inert gas for about 0.5 to about 2 hours or more.

6. The process of claim 5, wherein step a) is carried out at a temperature between about 350° C. and about 500° C. for a contact time of about 1 s to about 5 min and for a length of time of about 1 hour to about 10 hour, and wherein step a) is optionally followed by contacting the catalyst with an inert gas for about 0.5 to about 2 hours or more.

7. The process of claim 1, wherein step b) is carried out at a temperature between about 100° C. and about 600° C. for a contact time of about 0.0001 seconds to about 300 hours and for a length of time of about 0.01 seconds to about 150 hours, and wherein step b) is optionally followed by contacting the catalyst with an inert gas for about 0.5 to about 2 hours or more.

8. The process of claim 7, wherein step b) is carried out at a temperature between about 200° C. and about 500° C. for a contact time of about 0.001 seconds to about 100 hours and for a length of time of about 2 hours to about 30 hours.

9. The process of claim 8, wherein step b) is carried out at a temperature between about 350° C. and about 450° C. for a contact time of about 0.01 seconds to about 50 hours and for a length of time of about 5 hours to about 15 hours.

10. The process of claim 1, wherein the reaction is carried out in the presence of a source of oxygen.

11. The process of claim 1, wherein the reaction is carried out at a temperature from about 100° C. to about 750° C. and at a pressure from about 0.001 to about 100 atm for a contact time from about 0.1 second to about 1 hour.

12. The process of claim 11, wherein the reaction is carried out at a temperature from about 300° C. to about 600° C. and at a pressure from about 0.01 to about 20 atm for a contact time from about 0.1 second to about 1 hour.

13. The process of claim 12, wherein the reaction is carried out at a temperature from about 400° C. to about 500° C. and at a pressure from about 0.5 to about 5 atm for a contact time from about 1 second to about 10 min.

14. The process of claim 1, wherein the gas used in step a) and the gas used in step b) are diluted with an inert gas.

15. The process of claim 1, wherein the gas used in treating after the reaction is pure or diluted hydrogen or hydrogen fluoride.

16. The catalyst regeneration process of claim 3, wherein the gas used in treating after the reaction is nitrogen.

17. The process of claim 1, wherein the catalyst is supported.

18. The process of claim 1, wherein the catalyst is selected from the group consisting of an alkali metal, an alkaline earth metal, a transition metal, a rare earth metal, a salt of any of the foregoing, and any combination of the foregoing.

19. The process of claim 18, wherein the catalyst is an alkali metal.

20. The process of claim 1, wherein said fluoroiodoalkane is a combination of trifluoroiodomethane and pentafluoroiodoethane.

21. The process of claim 1, wherein the compound represented by the formula $CF_3(CF_2)_n$—Y is selected from the group consisting of $CF_3H$, $CF_3CF_2H$, $CF_3COOH$, $CF_3Cl$, $CF_3Br$, and any combination thereof.

22. The process of claim 21, wherein the compound is $CF_3H$.

23. The process of claim 1, wherein the source of iodine is a compound selected from the group consisting of $I_2$, HI, ICl, $IF_5$, $CI_4$, and combinations thereof.

24. The process of claim 23, wherein the source of iodine is $I_2$.

25. A process for the preparation of a fluoroiodoalkane represented by the structural formula $CF_3(CF_2)_n$—I wherein n is 0 or 1, comprising:

reacting a source of iodine with a compound represented by the structural formula $CF_3(CF_2)_n$—Y wherein Y is selected from H, Cl, Br and COOH and wherein n is 0 or 1, wherein the reaction is carried out at a temperature and at a pressure and for a contact time in the presence a catalyst sufficient to prepare the fluoroiodoalkane, and wherein the catalyst is subject to one or both of the following steps:
  a) treating the catalyst prior to the reaction via contact with a gas containing oxygen at a temperature and for a contact time sufficient to reduce the length of the induction period of the catalyst; and
  b) treating the catalyst after the reaction via contact with a gas containing oxygen or air at a temperature and for a contact time sufficient to regenerate the catalyst.

26. The process of claim 1, wherein the source of iodine is diluted in a diluent selected from the group consisting of nitrogen, helium, argon, CO, $CO_2$, water, an organic solvent, and combinations thereof.

27. The process of claim 1, wherein the catalyst is subject to both steps a) and b), wherein step b) is repeated, wherein the reaction is carried out at a temperature from about 100° C. to about 750° C. and at a pressure from about 0.001 to about 100 atm for a contact time from about 0.1 second to about 1 hour.

28. The process of claim 1, wherein the catalyst is subject to both steps a) and b), wherein step b) is repeated, wherein the reaction is carried out at a temperature from about 300° C. to about 600° C. and at a pressure from about 0.01 to about 20 atm for a contact time from about 0.1 second to about 1 hour.

29. The process of claim 1, wherein the catalyst is subject to both steps a) and b), wherein step b) is repeated, wherein the reaction is carried out at a temperature from about 400° C. to about 500° C. and at a pressure from about 0.5 to about 5 atm for a contact time from about 1 second to about 10 min.

30. The process of claim 25, wherein the source of oxygen is a compound selected from the group consisting of $O_2$, air, $O_3$, $N_2O$, $H_2O_2$, and combinations thereof.

31. The process of claim 25, wherein the gas containing oxygen used in treating after the reaction, further includes hydrogen, fluorine, or hydrogen fluoride.

32. The process of claim 25, wherein the gas containing oxygen used in treating after the reaction, further includes nitrogen.

* * * * *